United States Patent
Oaknin et al.

(10) Patent No.: US 7,881,514 B2
(45) Date of Patent: Feb. 1, 2011

(54) SYSTEM FOR IMAGE RECONSTRUCTION

(75) Inventors: Jacob Oaknin, Haifa (IL); Shoulamit Cohen Shwartz, Atlit (IL)

(73) Assignee: Ultraspect Ltd., Haifa (IL)

( * ) Notice: Subject to any disclaimer, the term of this patent is extended or adjusted under 35 U.S.C. 154(b) by 347 days.

(21) Appl. No.: 11/913,392

(22) PCT Filed: May 1, 2006
(Under 37 CFR 1.47)

(86) PCT No.: PCT/IL2006/000520
§ 371 (c)(1),
(2), (4) Date: Nov. 18, 2008

(87) PCT Pub. No.: WO2006/117781
PCT Pub. Date: Nov. 9, 2006

(65) Prior Publication Data
US 2009/0220129 A1 Sep. 3, 2009

Related U.S. Application Data

(60) Provisional application No. 60/676,311, filed on May 2, 2005.

(51) Int. Cl.
*G06K 9/00* (2006.01)
(52) U.S. Cl. .................. 382/128; 382/130; 382/131; 382/205; 382/270; 382/275; 250/208.1; 250/363.02
(58) Field of Classification Search .............. 382/128, 382/130, 131, 265, 270, 205, 190, 275; 250/363.02, 250/363.03, 363.04, 208.1; 717/159; 714/785; 378/4, 21; 702/181
See application file for complete search history.

(56) References Cited

U.S. PATENT DOCUMENTS

| 5,912,993 | A | 6/1999 | Puetter et al. |
| 6,353,688 | B1 | 3/2002 | Puetter et al. |

(Continued)

FOREIGN PATENT DOCUMENTS

WO   WO-02/12918   2/2002

(Continued)

OTHER PUBLICATIONS

U.S. Appl. No. 60/676,311, filed May 2, 2005.

(Continued)

*Primary Examiner*—Samir A. Ahmed
*Assistant Examiner*—Ali Bayat
(74) *Attorney, Agent, or Firm*—Fish & Richardson P.C.

(57) ABSTRACT

A method for imaging, including counting quanta of energy emitted into a range of angles from particles of an energy emitter distributed over a volume in a body, thereby generating a set of counts. The method further includes defining a probability distribution expression that specifies a local concentration of the particles of the energy emitter over the volume as a function of the set of counts, the function being defined in terms of respective coefficients of a plurality of different scales of the local concentration, including at least a first and a second scale. A dependence of the coefficients of the first scale on the coefficients of the second scale is specified, and the local concentration over the volume is computed by applying the probability distribution expression to the set of counts subject to the specified dependence.

23 Claims, 4 Drawing Sheets

U.S. PATENT DOCUMENTS

| | | | |
|---|---|---|---|
| 6,490,374 | B2 | 12/2002 | Puetter et al. |
| 6,895,125 | B2 * | 5/2005 | Puetter et al. ............... 382/265 |
| 6,943,355 | B2 * | 9/2005 | Shwartz et al. ......... 250/363.04 |
| 6,943,694 | B1 | 9/2005 | Ellis |
| 7,321,122 | B2 * | 1/2008 | Bryman ................ 250/363.03 |
| 2005/0234530 | A1 | 10/2005 | Takashino et al. |
| 2008/0260228 | A1 * | 10/2008 | Dichterman et al. ........ 382/131 |

FOREIGN PATENT DOCUMENTS

| | | |
|---|---|---|
| WO | WO-2004/113951 | 12/2004 |

OTHER PUBLICATIONS

Metz et al., "The geometric transfer function component for scintillation camera collimators with straight parallel holes," *Phys. Med. Biol.*, 1980; 25(6): 1059-1070.

Mallat, "A Theory for Multiresolution Signal Decomposition: The Wavelet Representation," *IEEE Transactions on Pattern Analysis and Machine Intelligence*, 1989; 11(7): 674-693.

Simoncelli and Adelson, "Noise removal via Bayesian wavelet coring," *Proceedings of 3rd IEEE International Conference on Image Processing*, 1996; 1: 379-382.

Abramovich et al., "Wavelet thresholding via a Bayesian approach," *J. R. Statist. Soc. B*, 1998; 60: 725-749.

Acar and Vogel, "Analysis of bounded variation penalty methods for ill-posed problems," *Inverse Problems 10*, 1994; 1217-1229.

Jaynes, "Prior Information and Ambiguity in Inverse Problems," *SIAM-AMS Proceedings*, 1984; 14; 151-166.

Geman and Geman, "Stochastic Relaxation, Gibbs Distributions, and the Bayesian Restoration of Images," *IEEE Transactions on Pattern Analysis and Machine Intelligence*, 1984; PAMI-6(6): 721-741.

Byrd et al., "A limited memory algorithm for bound constrained optimization," SIAM Journal of Scientific and Statistical Computing, 1995; 16(5): 1190-1208.

Byrd et al., "Representations of quasi-Newton matrices and their use in limited memory methods," *Mathematical Programming*, 1994;63(4); 129-156.

More and Thuente, "Line search algorithms with guaranteed sufficient decrease," *ACM Transactions on Mathematical Software*, 1994; 20(3): 286-307.

Donoho and Johnstone, "Adapting to Unknown Smoothness via Wavelet Shrinkage," Stanford University, Jul. 20, 1995.

Nowak, R.D. et al., "Platelets: a multiscale approach for recovering edges and surfaces in photon-limited medical imaging," IEEE Transactions on Medical Imaging, IEEE Service Center, Piscataway, NJ US vol. 22, No. 3, Mar. 1, 2003.

Willett, R.M. et al., "Fast multiresolution photon-limited image reconstruction," Biomedical Imaging: Marco to Nano, 2004, IEEE International Symposium on Arlington, VA, USA, Apr. 15, 2004.

Willett, R.M. et al., "Multiscale likelihood analysis and image reconstruction," Proceedings of the SPIE—The International Society for Optical Engineering SPIE-INT. Soc. Opt. ENG USA, vol. 5207, No. 1, Nov. 14, 2003.

* cited by examiner

US 7,881,514 B2

SYSTEM FOR IMAGE RECONSTRUCTION

CROSS-REFERENCE TO RELATED APPLICATION

This application is the U.S. national phase of International Application No. PCT/IL2006/000520, filed May 1, 2006, which claims the benefit of U.S. Provisional Patent Application No. 60/676,311 filed May 2, 2005, both of which are incorporated herein by reference in their entirety. The International Application published in English on Nov. 9, 2006 as WO 2006/117781 under PCT Article 21(2).

FIELD OF THE INVENTION

The present invention relates generally to image processing, and specifically to imaging using single photon emission sources.

BACKGROUND OF THE INVENTION

Methods for imaging an object emitting photons suffer from a number of limitations, especially in the case where the object is a human patient, or a section of the patient. The photon emitter is typically a radiopharmaceutical that is injected into, or inhaled by, the patient. In order to minimize deleterious effects on the patient, the quantity of photon emitter, the time during which the emitter is active, and the number of photons emitted, all need to be minimal. Furthermore, detected, detection systems for the photons typically have minimal or no focusing ability. Common detection systems may rely on the equivalent of a fly's eye detection system, wherein the photons are collimated along tubular channels before detection. As one amongst a number of further complications, the object being imaged is typically three-dimensional, but if a collimator is used the detection system has at best only a very approximate way of determining from where, along an axis or within a cone of view of the collimator, a detected single photon has been emitted.

Geometric factors for fly's eye collimators may be calculated. In a paper by Metz et al., entitled "The Geometric transfer function component for scintillation camera collimators with straight parallel holes," Phys. Med. Biol., 1980, v. 25, p. 1059-1070, the authors develop a method for predicting a geometric transfer function component for conventional scintillation camera collimators. The paper is incorporated herein by reference. In U.S. Pat. No. 6,943,355, to Shwartz, et al., whose disclosure is incorporated herein by reference, a method is described that enables a collimator to usefully detect photons from incident angles exceeding 5°.

Thus, geometric factors may be allowed for, given a scan time that is sufficiently long. However, the scan time is critical, since the long scan time needed by the imaging system means that the patient is exposed for the same long time. Unfortunately, raw data produced by operating at shorter times, or with reduced concentrations of radioactivity to produce the same benefit, has a lower signal to noise ratio than at the longer times. This acquired raw data is insufficient to enable a good reconstruction of local concentrations of the radiopharmaceutical, which is the goal of the imaging system, so that reconstructed images at the shorter times or with reduced concentrations are of extremely low quality.

Regularization, i.e., reformulation of the raw data, may be used to derive images from the raw data. For example, U.S. Pat. Nos. 5,912,993, 6,353,688, and 6,490,374 to Puetter et al., whose disclosures are incorporated herein by reference, describe methods for planar image reconstruction using "Pixon" elements and bases, which are respectively defined as indivisible units of information and sets of possible functions from which the elements are selected.

Wavelet theory may also be used for regularization as described, for example, by Mallat, in a paper entitled "A theory for multiresolution signal decomposition: the wavelet representation," IEEE Trans. Pat. Anal. Mach. Intell., vol. 11, pp. 674-693, 1989, and by Simoncelli et al., in a paper entitled, "Noise removal via Bayesian wavelet coring," 3rd IEEE Int'l. Conf. Image Processing, Lausanne, Switzerland, September 1996, vol. 1, pp. 379-382, IEEE Sig. Proc. Society. Both of these papers assume a Laplacian wavelet distribution. A paper entitled, "Wavelet thresholding via a Bayesian approach," by Abramovich et al., J. R. Statist. Soc. B, vol. 60, pp. 725-749, 1998, describes a variation on this process, wherein a threshold is set to the wavelet coefficients. The above papers are incorporated herein by reference.

SUMMARY OF THE INVENTION

In embodiments of the present invention, an energy emitter such as a radiochemical is distributed over a specific region, typically within the body of a patient. A camera for imaging the region measures numbers of energy quanta from the emitter that are received at the camera. The measurements produce a set of counts over multiple angles subtended by the camera at the specific region. An optimization objective function of local concentration of particles of the emitter is defined as a function of the set of counts and of a number of parameters associated with the camera, including the geometric configuration of the camera.

The optimization objective function is rewritten as a probability distribution expression. This expression is defined in part in terms of respective wavelet coefficients of a plurality of different "scales" of the local concentrations at different locations of the specific region. The locations are mapped in multiple dimensions. The term scale corresponds to a scaling factor applied to location coordinates along all the dimensions. A dependence between the coefficients of the different scales is defined. A processing unit analyzes the set of counts using the expression and the predefined inter-scale dependence, and thus determines values of the local concentrations having the highest probability in view of the collected counts. The values correspond to a three-dimensional image of local concentration of the energy emitter within the region. By assuming the predetermined dependence for the scale coefficients, the image produced by the expression analysis is significantly improved in quality compared to images from expressions that do not assume a dependence. In cases where the energy emitter is a radiochemical, the improvement allows for significant reductions in exposure time to the radiochemical and/or the amount of radiochemical injected into the patient.

In one embodiment, the predetermined dependence sets a ratio of the coefficients of sequential scales to be equal to the expression $$\frac{s^2}{(s+1)^2},$$

wherein s is a cardinality of the wavelet scale.

Typically, the probability distribution expression is defined in terms of a mixture of stationary Gaussian and Poisson distributions relating the measured set of counts to an expected set of counts. The expected set of counts is determined from, inter alia, the geometric configuration of the camera. In a disclosed embodiment, for each of the set of counts, the variance of the distribution is equated to the maximum of the count value and a user-determined constant.

In some embodiments of the present invention, the probability distribution expression is defined in terms of the Haar wavelet. Using the Haar wavelet enables the wavelet coefficients and their dependence to be formulated simply, and allows the processing unit to perform the required analysis in an efficient manner.

In an alternative embodiment, characteristics of elements in the specific region, such as the motion or viability of the elements, are determined by measuring the local concentrations as they change with time. Values of the measured local concentrations at different times may be adjusted so that a mean of the measured local concentrations corresponds to an expected mean. The expected mean is derived from total counts over the whole time of measurement.

There is therefore provided, according to an embodiment of the present invention, a method for imaging, including:

counting quanta of energy emitted into a range of angles from particles of an energy emitter distributed over a volume in a body, thereby generating a set of counts;

defining a probability distribution expression that specifies a local concentration of the particles of the energy emitter over the volume as a function of the set of counts, the function being defined in terms of respective coefficients of a plurality of different scales of the local concentration, including at least a first and a second scale;

specifying a dependence of the coefficients of the first scale on the coefficients of the second scale; and computing the local concentration over the volume by applying the probability distribution expression to the set of counts subject to the specified dependence.

Typically, the dependence includes a first cardinality of the first scale and a second cardinality of the second scale.

The first scale and the second scale may include sequential scales, and the dependence may be given by:

$$\alpha_s = \frac{s^2}{(s+n)^2}$$

wherein s represents a cardinality of the first scale, $0.5 \leq n \leq 1.5$, and wherein $\alpha_s$ represents the dependence.

In one embodiment an argument of the function comprises a term:

$$(\theta_i^s - \alpha_s \theta_i^{s+1}),$$

wherein:
i is an index of a location of the particles;
s and s+1 are respective cardinalities of the first and second scales;
$\theta_i^s, \theta_i^{s+1}$ represent respective coefficients of the first and second scales; and
$\alpha_s$ is a function of s.

In an alternative embodiment $$f_s(z) = \frac{\|z\|_2^r}{s^r \sigma}$$

wherein:
$f_s(z)$ represents the function, having an argument z;
s is a cardinality of the first scale;
r is a positive number; and
σ is a constant.

In some embodiments $$z = (\theta_i^s - \alpha_s \theta_i^{s+1}),$$

wherein:
i is an index of a location of the particles;
s+1 is a cardinality of the second scale;
$\theta_i^s, \theta_i^{s+1}$ represent respective coefficients of the first and second scales; and
$\alpha_s$ is a function of s.

Typically, the probability distribution expression includes a term $$-\log [P(X)],$$

wherein $$-\log[P(X)] = \sum_s \sum_i f_s(\theta_i^s - \alpha_s \theta_i^{s+1}),$$

and wherein:
X is a vector representing the local concentration;
$f_s(.)$ represents the function;
i is an index of a location of the particles;
s and s+1 are respective cardinalities of the first and second scales;
$\theta_i^s, \theta_i^{s+1}$ represent respective coefficients of the first and second scales; and
$\alpha_s$ is a function of s.

Alternatively or additionally, the probability distribution expression includes a term $$-\log [P(Y|X)],$$

wherein $$-\log[P(Y \mid X)] = \frac{1}{2} \sum_{b=1}^{b_M} \frac{(y_b - (HX)_b)^2}{\Delta_b},$$

and wherein:
b is an index representing bins receiving the set of counts;
$b_M$ is a total number of the bins;
$y_b$ is a count received at a bin b;
$(HX)_b$ is an expected number of counts for the bin b
Y is a vector representing the set of counts;
X is a vector representing the local concentration; and
$\Delta_b$ is a variance for the bin b. Typically, $$\Delta_b = \max(y_b, B),$$

wherein B is a constant.

The probability distribution expression may include a term having a distribution chosen from a Poisson distribution, a Laplacian distribution, and a non-white Gaussian distribution.

Typically, the coefficients include wavelet coefficients of a Haar wavelet.

In a disclosed embodiment, computing the local concentration includes performing an iteration on the probability distribution expression to find a maximum value of a probability distribution in the expression.

In some embodiments the local concentration includes a plurality of time-dependent-local-concentrations including a first time-dependent-local-concentration measured at a region of the volume during a first time slot and a second time-dependent-local-concentration, different from the first time-dependent-local-concentration, measured at the region during a second time slot, and the probability distribution expression includes a time-dependent regularization function relating the first time-dependent-local-concentration and the second time-dependent-local-concentration.

The time-dependent regularization function typically includes a Fourier transform of a sequence of time-dependent-local-concentrations at the region, the sequence including the first time-dependent-local-concentration and the second time-dependent-local-concentration.

The method typically also includes synchronizing at least one of the first time slot and the second time slot in response to a time-dependent signal received from the body. Typically, computing the time-dependent-local-concentrations includes iteratively computing partial sums of the time-dependent-local-concentrations.

In some disclosed embodiments the plurality of different scales includes a number of scales chosen from between three and seven scales, and is typically five scales.

In a further alternative embodiment, the probability distribution expression includes a conditional expectation.

There is further provided, according to an embodiment of the present invention, imaging apparatus, including:

a camera which is arranged to count quanta of energy emitted into a range of angles from particles of an energy emitter distributed over a volume in a body, thereby generating a set of counts; and a processing unit which is configured to:

define a probability distribution expression that specifies a local concentration of the particles of the energy emitter over the volume as a function of the set of counts, the function being defined in terms of respective coefficients of a plurality of different scales of the local concentration, including at least a first and a second scale, specify a dependence of the coefficients of the first scale on the coefficients of the second scale, and compute the local concentration over the volume by applying the probability distribution to the set of counts subject to the specified dependence.

Typically, the local concentration includes a plurality of time-dependent-local-concentrations including a first time-dependent-local-concentration measured at a region of the volume during a first time slot and a second time-dependent-local-concentration, different from the first time-dependent-local-concentration, measured at the region during a second time slot, and the apparatus includes:

a detector which detects a time-dependent signal from the body and which conveys the time-dependent signal to the processing unit so as to synchronize at least one of the first time slot and the second time slot.

There is further provided, according to an embodiment of the present invention, a computer software product for imaging, including a computer-readable medium having computer program instructions recorded therein, which instructions, when read by a computer, cause the computer to:

receive counts of quanta of energy emitted into a range of angles from particles of an energy emitter distributed over a volume in a body, thereby generating a set of counts, define a probability distribution expression that specifies a local concentration of the particles of the energy emitter over the volume as a function of the set of counts, the function being defined in terms of respective coefficients of a plurality of different scales of the local concentration, including at least a first and a second scale, specify a dependence of the coefficients of the first scale on the coefficients of the second scale, and compute the local concentration over the volume by applying the probability distribution expression to the set of counts subject to the specified dependence.

The present invention will be more fully understood from the following detailed description of the embodiments thereof, taken together with the drawings, a brief description of which follows.

DETAILED DESCRIPTION OF EMBODIMENTS

Figure 1:
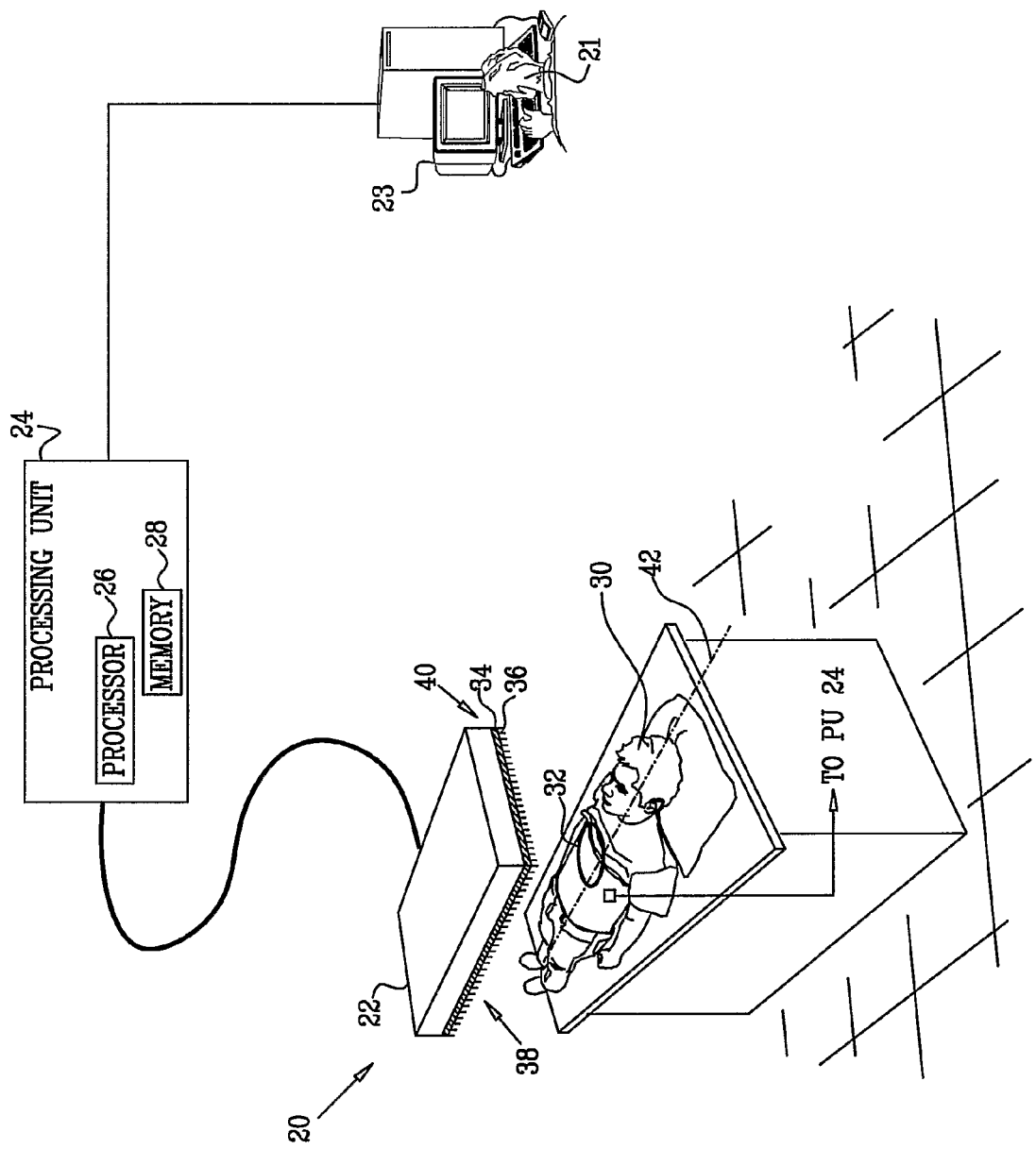
FIG. 1 is a schematic diagram of an imaging system, according to an embodiment of the present invention.

Embodiments of the present invention provide a method of image reconstruction for images that are generated by particles of energy emitters and detected by detectors at different locations. For example, in different aspects of the present invention, the energy emitter particles may comprise a radiochemical which emits electromagnetic (EM) energy by radioactive decay; an excited atom, such as is formed in a magnetic resonance environment, which emits EM energy by changing its energy state; or a molecule which emits sound energy in response to ultrasonic waves impinging on the molecule. The emitted energy may in all cases be assumed to be in the form of photons or phonons. In the specification and in the claims, the terms quanta or energy quanta are assumed to encompass both photons and phonons. In the specification and in the claims, the term energy emitter is assumed to encompass both active emitters such as the radiochemical exemplified above, and passive emitters, such as the molecule emitting sound energy as reflected ultrasound. The terms "camera" or "camera detector" refer to any sort of detection system suitable for measuring the emission of the quanta in question.

It will be understood that while the description below refers in general to a radiochemical as the energy emitter, the principles of the present invention are applicable, mutatis mutandis, to energy emitters of other types.

The problem of reconstructing local concentrations of particles of a radiochemical from the raw data generated by a camera is an example of an ill-posed inverse problem, in the sense that there may not be a single solution, and even if a single solution exists, it may be unstable with respect to small perturbations of the raw data results.

Methods for improving the quality of the results generated by the physical detection system described above have been sought. Some of these methods are based on the application of Bayes' Theorem:

$$P(I \mid D) = \frac{P(D \mid I) \cdot P(I)}{P(D)} \tag{1}$$

where D represents the raw data, I represents the image, P(I|D) is the probability of I given D, and P(I) is the probability of I.

An expression (2) derived from equation (1) is:

$$P(I|D) \propto P(D|I) \cdot P(I) \tag{2}$$

where the first term on the right side of the proportionality, measuring the likelihood of D given I, may be referred to as the likelihood term, and the second term may be referred to as the image prior, expressing an a priori expectation of a particular image.

The Bayesian approach to solving ill-posed inverse problems was first described by Jaynes in his paper "Prior Information and Ambiguity in Inverse Problems," Inverse Problems, D. W. McLaughlin (ed.), Am. Math. Soc., SIAM-AMS Proceedings vol. 14, 1984. Bayesian image reconstruction was first used by Geman et al. in their paper "Stochastic relaxation, Gibbs distributions, and the Bayesian restoration of images," IEEE Trans. PAMI, PAMI-6(6), November 1984. Both papers are incorporated herein by reference.

Earlier approaches at regularization of raw data use wavelets, and typically assume that results follow a Gaussian distribution. However, more recent attempts at regularization using wavelet theory have assumed other distributions.

The simplest wavelet, the Haar wavelet, is defined as:

$$h(x) = \begin{cases} 1 & 0 \leq x < \frac{1}{2} \\ -1 & \frac{1}{2} \leq x < 1 \\ 0 & \text{otherwise} \end{cases} \tag{3}$$

While being the simplest wavelet, the Haar wavelet has the disadvantage that it is discontinuous, and therefore not differentiable at the discontinuities.

Reference is now made to FIG. 1, which is a schematic diagram of an imaging system 20, according to an embodiment of the present invention. System 20 comprises a camera 22 coupled to a processing unit (PU) 24, which processes raw data received from the camera. PU 24 includes a processor 26 and a memory 28, wherein are stored software instructions for storing and processing the raw data. Processor 26 may be a general-purpose computer or may comprise hard-wired or programmable logic. In the event that processor 26 comprises a general-purpose computer the software may be provided as a computer software product in a tangible form on a computer-readable medium such as a CD-ROM, or as an electronic data transmission, or as a mixture of both forms.

In operating system 20, an energy emitter, herein assumed to be a radiochemical formed from a radioisotope such as $^{99m}$Tc or $^{123}$I, is injected into a patient 30, and gamma ray quanta emitted by the decay of the radioisotope are detected by camera 22. The raw data recorded by camera 22 is reconstructed by PU 24 to determine a three-dimensional map of the concentrations of the radioisotope, and hence of the radiochemical, in a section 32 of the body of patient 30 that is scanned by camera 22. PU 24 may display the three-dimensional map as a two-dimensional image on a graphic display unit 23, for viewing by an operator 21 of system 20.

Camera 22 comprises a detector 34 which is divided into a two-dimensional array 40 of pixels. Detector 34 typically comprises one or more scintillators followed by respective photo-multipliers. Alternative detectors which do not use photo-multipliers, such as solid-state detectors, are known in the art, and it will be appreciated that such detectors are within the scope of the present invention. In the following explanation, detector 34, by way of example, is assumed to use scintillators. Optionally, each scintillator may be configured to count gamma ray photons only within a specific energy range. The range may be defined so as to exclude energies of photons that may have undergone scattering. (Scattered photons typically have energies lower than unscattered photons.)

A collimating grid 36, before detector 34 comprises a plurality of collimators 38, typically in the form of closely packed hexagons, although the collimators may be any other type known in the art, such as cylinders or cones. Typically, array 40 of pixels is configured independently of collimators 38. Optionally, processing unit 24 uses collimators 38 to divide detector 34 into the array of detector pixels, and may allocate a group of contiguous collimators to one pixel. By way of example, array 40 is assumed to comprise a square array of 64×64 pixels, but it will be understood that the number of pixels, and their geometric arrangement and shape, may be different from that exemplified here, and may comprise any convenient number and geometry.

There are a number of methods, known in the art, by which camera 22 acquires its raw data. For example, camera 22 may be held stationary in relation to patient 30, may be continuously moved in relation to the patient, or the camera may be moved from one position to another, being held stationary at each position. Herein, by way of example, an operator of system 20 is assumed to rotate camera 22 in a 180° arc of a circle, perpendicular to an axis 42 of patient 30, and the camera is held stationary at sixty positions separated by 3° on the arc. The camera records its raw data at the sixty different positions. Camera 22 thus generates 64×64×60=245,760 values of raw data. In an alternative embodiment, the camera records 64 sets of data, generating $64^3$=262,144 values of raw data. However, it will be understood that the total number of values of raw data depends on the number of pixels defined for camera 22, as well as on the number of positions of the camera, and that substantially all such numbers are within the scope of the present invention. It will also be understood that the raw data may be acquired by substantially any method known in the art, and that all such methods are assumed to be comprised within the scope of the present invention.

PU 24 receives the raw data, and processes it to find concentrations of the radiochemical in section 32. The raw data is herein represented as a vector $Y=\{y_b\}$, where b is a raw data bin index from 1 to $b_M$, and where $b_M$ represents the total number of values of raw data. Optionally, raw data Y may be pre-processed by PU 24 before being analyzed as described below. Such pre-processing is well known in the art, and typically includes rearrangement of actual numbers of counts detected by detector 34 into bins b, noise reduction, and/or detector distortion compensation, etc.

In the computation that follows, section 32 is taken to comprise a cube formed of $64^3$, 262,144, voxels. Each voxel is a cube having a pre-determined edge length, which is assumed by way of example to be approximately 0.68 cm. It will be appreciated, however, that section 32 and/or the voxels forming the section may have a geometric shape different from a cube; for example the section and/or the voxels may be box-shaped, with the edges of the box having different values;

it will also be appreciated that the number of voxels within section 32, and the size of the voxels, may be different from the values exemplified herein.

The concentration of particles of radiochemical in section 32 is herein represented as a vector $X=\{x_i\}$, where i is an index from 1 to $v_T$, and where $v_T$ represents the total number of voxels. It will be understood that elements $x_i$ of vector X are distributed in three spatial dimensions and that i determines a location of $x_i$.

Optionally, a detector 44 is coupled to patient 30, typically for the purpose of allowing PU 24 to correlate patient parameters measured by the detector with raw data Y. An example of the use of such a detector is described below with reference to FIG. 4.

Figure 2:
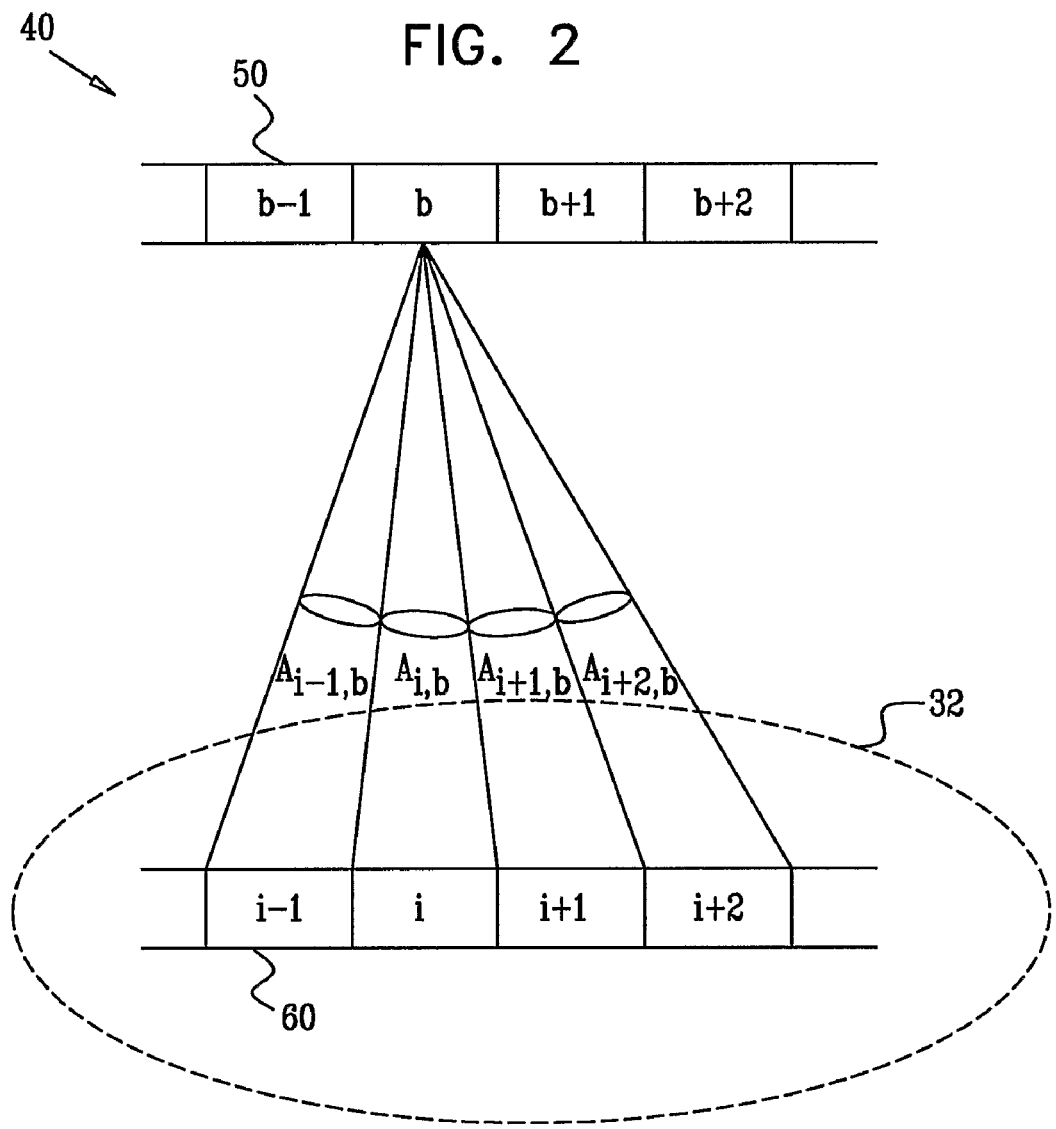
FIG. 2 is a schematic diagram illustrating geometric properties of a camera detector in the system of FIG. 1, according to an embodiment of the present invention.

FIG. 2 is a schematic diagram illustrating geometric properties of camera 22, according to an embodiment of the present invention. A section 50 of array 40, when camera 22 is in a given position, illustrates four bins b−1, b, b+1, b+2. Each bin corresponds to one of the pixels of array 40, for the given position of the camera. A portion 60 of section 32 includes four voxels i−1, i, i+1, i+2 of the section. Each voxel radiates gamma ray photons in proportion to the concentration of radiochemical in the voxel, but the number of photons detected by each of the bins, $y_{b-1}$, $y_b$, $y_{b+1}$, $y_{b+2}$, depends on factors other than the concentrations, including geometric factors. For example, solid angles $A_{i-1,b}$, $A_{i,b}$, $A_{i+1,b}$, $A_{i+2,b}$ are subtended by each of the voxels i−1, i, i+1, i+2 at bin b, and the number of photons detected by bin b is a function of the solid angles.

As will be apparent to those skilled in the art, other factors which may determine the number of photons detected by a specific bin include, but are not limited to, the following:

An effective area of the bin, which typically takes into account a blocking effect of collimators. Geometric effects of the collimators may be allowed for, as described in the Background of the Invention.

A probability that a photon may penetrate septa comprised in collimators of the bin.

Attenuation and/or scattering of photons due to interaction of the photons with media between the bin and a radiating voxel.

Energy of the emitted photons, since the energy may affect the values of effective area, probability, attenuation and scattering listed above, as well as a response function of detector 34.

A vector $\overline{Y}=\{\overline{y_b}\}$ represents an expected number of photons detected, in the absence of noise, in each bin b due to the factors described above. In embodiments of the present invention, we assume:

$$\overline{Y}=HX \quad (4)$$

where H is a matrix having coefficients $h_{b,i}$.

Coefficients $h_{b,i}$ take into account part or all of the factors described above. Following from equation (4) the notation $(HX)_b$ is also used for $\overline{y_b}$.

For specific data Y, we assume that the required value of each $x_i$ is given by:

$$\{x_i\}_{i=1}^{v_T}=\text{argmax}[P(X|Y)] \quad (5)$$

where P(X|Y) is the probability of the occurrence of X given Y.

In other words, the values of $x_i$ correspond to the vector X that has a maximum probability of occurring given the observed data Y.

From equation (1), P(X|Y) may be rewritten:

$$P(X|Y) = \frac{P(Y|X) \cdot P(X)}{P(Y)} \quad (6)$$

where P(X) and P(Y) are the respective probabilities of X and Y occurring.

By taking logarithms, we derive the following expressions from equation (6):

$$\log[P(X|Y)]=\log[P(Y|X)]+\log[P(X)]-\log[P(Y)] \quad (7)$$

Since Y is the data received by PU 24, log [P(Y)] is a constant, which, as is explained below, may be assumed to be 0 without loss of generality. Applying this to equation (7), and multiplying by −1, gives:

$$-\log[P(X|Y)]=-\log[P(Y|X)]-\log[P(X)] \quad (8)$$

Referring back to equation (5), finding the vector X having a maximum probability of occurring corresponds to finding the vector X that causes −log [P(X|Y)] to be a minimum. The terms on the right side of equation (8) are termed the likelihood term, −log [P(Y|X)], and the penalty term, −log [P(X)], and are analyzed separately below.

Likelihood Term, −log [P(Y|X)]

In an embodiment of the present invention, the values of $y_b$ are assumed to form an approximately Gaussian distribution, so that:

$$P(y_b|X) = e^{\frac{-(y_b-(HX)_b)^2}{2\Delta_b}} \quad (9)$$

where $\Delta_b$ is the variance of $y_b$.

From equation (9), assuming the terms are independent, the expression for the likelihood term becomes:

$$-\log[P(Y|X)] = \frac{1}{2}\sum_{b=1}^{b_M}\frac{(y_b-(HX)_b)^2}{\Delta_b} \quad (10)$$

In the present embodiment, $$\Delta_b = \max(y_b, B) \quad (11)$$

where B is a predetermined value.

Typically, the value of B is determined according to the actual values of $y_b$, and is a predetermined constant of the order of 200. The value of B is set to ensure that low values of $y_b$ do not unduly skew the value of the likelihood term. A method for determining B is described in reference to FIG. 3 below.

From equation (11), the expression for the likelihood term for the disclosed embodiment may be rewritten as:

$$-\log[P(Y|X)] = \frac{1}{2}\sum_{b=1}^{b_M}\frac{(y_b-(HX)_b)^2}{\max(y_b,B)} \quad (12)$$

It will be appreciated that expression (12) is one specific example of the derivation of the likelihood term, and that the term may be derived by a number of related methods, giving correspondingly different expressions. Examples of some alternative methods for deriving the likelihood term are as follows:

The variance $\Delta_b$ could be defined differently from equation (8) while still including a lower bound B and having a value that varies according to the bins. Examples of different expressions for $\Delta_b$ are $\sqrt{y_b^2 + B^2}$ or $(y_b + B)$; other such expressions will be apparent to those skilled in the art.

Rather than having a different variance for each bin b, the variance may be a value $\Delta$ that is the same for all bins.

Equation (9) assumes an approximately Gaussian distribution; other distributions which may be used include a Poisson distribution, a mixture of a Gaussian and a Poisson distribution, a Laplacian distribution, or a non-white Gaussian distribution. In the latter case, the expected value $(HX)_b$ may be assumed to be weighted according to expected values from neighboring bins, such as $(HX)_{b-1}$ and/or $(HX)_{b+1}$.

Other derivations for the likelihood term will be apparent to those having skill in the art, and all such derivations are assumed to be comprised within the scope of the present invention.

Penalty Term, $-\log[P(X)]$

The inventors have found that writing the penalty term in terms of wavelet coefficients, where the coefficients at different scales are set to be dependent on each other, results in reconstruction of generally clearer images than are produced by prior art systems. A specific example of such a dependency is described in more detail hereinbelow.

A general expression for the penalty term is defined as:

$$-\log[P(X)] = \sum_s \sum_{i \in Z^3} f_s(\theta_i^s - \alpha_s \theta_i^{s+1}) \quad (13)$$

where $f_s(.)$ is a function;

s are positive integers representing a cardinality of the scale of the wavelet;

i correspond to the indices, defined above, for vector X; herein $i \equiv (n_1, n_2, n_3) \in Z^3$ are ordered triples of integers $n_1$, $n_2$, $n_3$, identifying the voxels of X;

$\theta_i^s, \theta_i^{s+1}$ are wavelet coefficients; and $\alpha_s$, where $\alpha_s \in R | \alpha_s > 0$, is a term relating the dependency of sequential wavelet coefficients.

Expression (13) is evaluated in three dimensions (the three spatial dimensions of vector X), so that the ordered triples i, which have values from (1, 1, 1) to (64, 64, 64), cover these spatial dimensions. Thus, $\theta_i^s$ is a three dimensional vector which may be written:

$$\theta_i^s = \{\theta_{i,d}^s, d=1,2,3\} \quad (14)$$

The wavelet used herein, by way of example, is the Haar wavelet, defined in equation (3). The properties of the Haar wavelet allow us to rewrite the elements of wavelet coefficients $\theta_i^s$ in terms of elements $x_i$ as follows:

$$\theta_{i,d}^s = \sum_{m=0}^{s-1} x_{i+m \cdot j_d} - \sum_{m=-s}^{-1} x_{i+m \cdot j_d} \quad (15)$$

where $\{j_d, d=1, 2, 3\}$ is an orthonormal standard basis in $Z^3$.

In this embodiment, the following limitations are placed on the expression for the penalty term:

1. The dependency term $\alpha_s$ is defined in terms of the cardinality of the scale:

$$\alpha_s = \frac{s^2}{(s+n)^2} \quad (16)$$

where $0.5 \leq n \leq 1.5$. Herein it is assumed that $n=1$.

The argument of function $f_s(.)$ (equation 13) is $(\theta_i^s - \alpha_s \theta_i^{s+1})$, and expressions for $\theta_{i,d}^s$ and $\alpha_s$, as defined by equations (15) and (16), enable us to evaluate the argument for predefined functions of x.

2. The function $f_s(.)$ is assumed to be of the form:

$$f_s(z) = \frac{\|\|z\|_2\|^r}{s^r \sigma} \quad (17)$$

Thus, $$f_s(\theta_i^s - \alpha_s \theta_i^{s+1}) = \frac{\|\|\theta_i^s - \alpha_s \theta_i^{s+1}\|_2\|^r}{s^r \sigma} \quad (18)$$

where $\sigma$ is a constant, and $r > 0$. Herein, r is assumed equal to 1.

The Penalty term may thus be written:

$$-\log[P(X)] = \frac{1}{\sigma} \sum_s \sum_{i \in Z^3} \frac{\|(\theta_i^s - \alpha_s \theta_i^{s+1})\|_2}{s} \quad (19)$$

Returning to equation (8), from equations (12) and (19) the expression for $-\log[P(X|Y)]$ may be rewritten:

$$-\log[P(X|Y)] = \quad (20)$$

$$\frac{1}{2} \sum_{b=1}^{b_M} \frac{(y_b - (HX)_b)^2}{\max(y_b, B)} + \frac{1}{\sigma} \sum_s \sum_{i \in Z^3} \frac{\|\theta_i^s - \alpha_s \theta_i^{s+1}\|_2}{s}$$

Inspection of equation (20) shows that the value of $-\log[P(X|Y)]$ depends on two factors, B and $\sigma$, which may be set by experimentation. An exemplary method for determining B and $\sigma$ is described below with reference to FIG. 3. From equation (20), the value of $-\log[P(X|Y)]$ also depends, inter alia, on the number of scales s summed in the Penalty term. The inventors have found that summing values of s between 1 and 5, as shown in equation (21) below, gives a satisfactory result. Other ranges of values for s include values between 1 and 3, and values between 1 and 7. However, those skilled in the art will be able to evaluate alternative ranges for s without undue experimentation, and all such ranges are assumed to be within the scope of the present invention.

If scales s are summed between 1 and 5, equation (20) may be rewritten as the expression:

$$-\log[P(X|Y)] = \quad (21)$$

-continued $$\frac{1}{2}\sum_{b=1}^{b_M} \frac{(y_b - (HX)_b)^2}{\max(y_b, B)} + \frac{1}{\sigma}\sum_{s=1}^{s=5}\sum_{i \in Z^3} \frac{\|(\theta_i^s - \alpha_s \theta_i^{s+1})\|_2}{s}$$

Embodiments of the present invention determine values of $x_i$ that minimize $-\log [P(X|Y)]$ and thus maximize $P(X|Y)$. (Returning briefly to equation (7), since the term $\log [P(Y)]$ of equation (7) is a constant, and since we find a minimum of $-\log [P(X|Y)]$, the term $\log [P(Y)]$ may be assumed to be 0 without loss of generality.)

The determination of the minimum may be performed using any suitable algorithm known in the art for finding minima of functions of the type exemplified by equation (20), including both iterative and non-iterative algorithms.

One such iterative algorithm, which the inventors have found performs efficiently, is a limited-memory quasi-Newton algorithm. The algorithm is described in "A limited memory algorithm for bound constrained optimization," SIAM Journal of Scientific and Statistical Computing, 16, 5, pp. 1190-1208, 1995; and "Representations of quasi-Newton matrices and their use in limited memory methods," Mathematical Programming, 63, 4, pp. 129-156, 1994, both papers by Byrd et al., whose disclosures are incorporated herein by reference. A part of the algorithm is also described in "Line search algorithms with guaranteed sufficient decrease," ACM Transactions on Mathematical Software 20 (1994), no. 3, pp. 286-307, by Mor'e et al., whose disclosure is incorporated herein by reference. In one embodiment of the present invention, the algorithm is run a preset number of times before stopping. Other suitable stopping criteria, such as evaluating a rate of convergence, will be apparent to those of skill in the art.

The algorithm that determines the minimum of $-\log [P(X|Y)]$ returns a value for X, corresponding to a three-dimensional image of section 32. Hereinbelow, the algorithm used is termed the minimum-finding algorithm. Typically, after using the minimum-finding algorithm, system 20 presents the three-dimensional image as two-dimensional slices on unit 23. Optionally, prior to presentation on unit 23, processing unit 24 may post-process the values of X derived from the minimum-finding algorithm.

In an alternative embodiment of the present invention, a maximum for a conditional expectation $E(X|Y)$, is found. $E(X|Y)$ is defined as follows:

$$E(X|Y) = \frac{\int_{x_j \geq 0, j \in Z^3} X \cdot P(X|Y) dX}{\int_{x_j \geq 0, j \in Z^3} P(X|Y) dX} \quad (22)$$

where $P(X|Y)$ may be found from the expression for $-\log [P(X|Y)]$ given in equation (21).

Methods used to find the maximum of $E(X|Y)$ are generally similar to those for finding the maximum for $P(X|Y)$, described herein.

Figure 3:
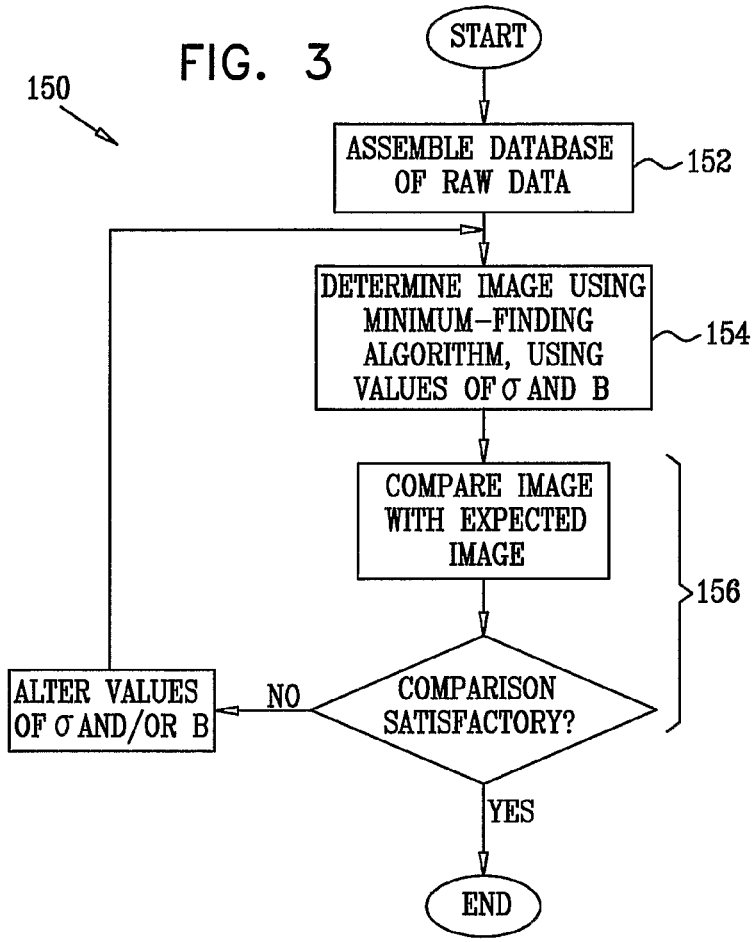
FIG. 3 is a flowchart illustrating steps for determining constants in the system of FIG. 1, according to an embodiment of the present invention.

FIG. 3 is a flowchart 150 illustrating steps for determining $\sigma$ and B, used in equation (21), according to an embodiment of the present invention. Before implementing the minimum-finding algorithm, the constants $\sigma$ and B are determined, typically by a method similar to flowchart 150. In an initial step 152 of the flowchart, a database of raw data is assembled. Typically the database comprises $\{y_b\}$ values taken from patients. In one implementation of flowchart 150, the inventors used values of $\{y_b\}$ from 26 patients. Alternatively or additionally, the database comprises $\{y_b\}$ values from a phantom, which correspond in quality, e.g., count number, to patient data.

In a step 154, a first image is determined from $\{y_b\}$ by applying the minimum-finding algorithm to equation (21), using initial values for $\sigma$ and B.

In a comparison step 156, the first image is compared with an expected image. For data such as that from a phantom, the expected image may be deduced from the known geometric distribution of the radiochemical; alternatively, the expected image may be determined by using a large quantity of radiochemical and/or a long exposure time to improve the quality of the results presented to PU 24. For data such as those from patients, one or more expert physicians may generate the expected image. If the comparison is satisfactory, flowchart 150 ends. If the comparison is unsatisfactory, the flowchart returns to step 154, and $\sigma$ and/or B are changed.

Steps 154 and 156 reiterate until a satisfactory comparison is achieved in step 156.

The inventors have found that in one embodiment of the present invention, flowchart 150 generated values for $\sigma$ and B equal to 1000 and 200 respectively.

Figure 4:
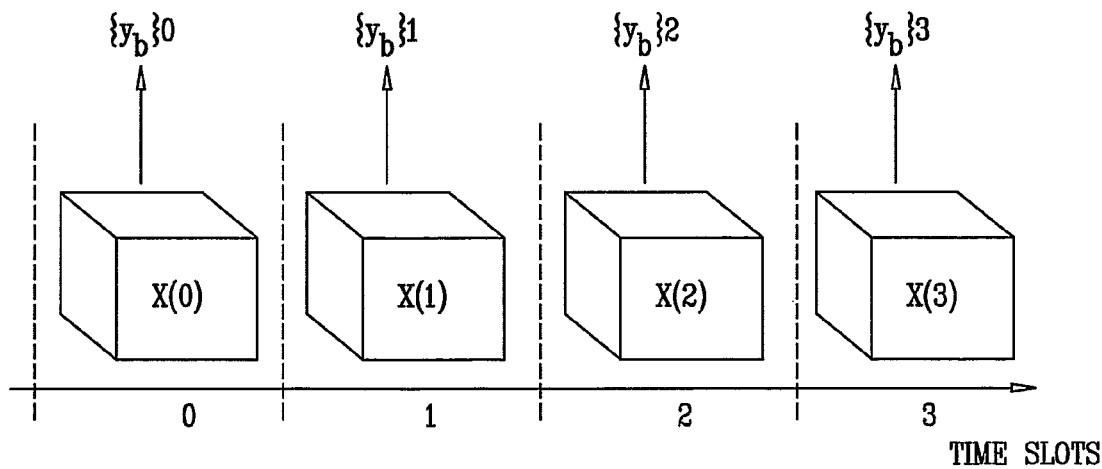
FIG. 4 is a schematic diagram illustrating changes in an image generated by the system of FIG. 1 with respect to time, according to an embodiment of the present invention.

FIG. 4 is a schematic diagram illustrating changes in X with respect to time t, according to an embodiment of the present invention. The description above does not explicitly incorporate time in finding values of X, although in fact X typically does vary with time due to the decay of the radiochemical itself. In addition, depending on where section 32 is located in the body of patient 30, and/or of the malady being imaged, there may be a variation of X with time due to, inter alia, movement of parts of the body. This variation may be periodic, non-periodic, or a combination of the two. For example, if section 32 comprises the heart, there is a periodic change in X due to the heart beating. If section 32 comprises a blood vessel, there is movement of blood through the vessel, and the movement may comprise a combination of periodic motion and translation of the blood. As a further example, over time, necrotic tissue may display differently compared to viable tissue. FIG. 4 illustrates the changes of X with time by assuming that there are a number of discrete values of X, represented by X(t), at time slots t=0, 1, 2, . . . . Each X(0), X(1), X(2), . . . , generates respective results $\{y_b\}_0$, $\{y_b\}_1$, $\{y_b\}_2$, . . . . Herein X(0), X(1), X(2), . . . , are also termed gated values of X, and $\{y_b\}_0$, $\{y_b\}_1$, $\{y_b\}_2$, . . . are also termed gated values of Y.

In one embodiment of the present invention, the values of X(0), X(1), X(2), . . . are determined substantially independently of each other, so that essentially any relation between the different values is ignored. The determinations are by applying the minimum-finding algorithm to each set of values $\{y_b\}_0$, $\{y_b\}_1$, $\{y_b\}_2$, . . . .

In an alternative embodiment of the present invention, sequential values X(0), X(1), X(2), . . . are assumed to have a relation to each other. The following description uses the periodic motion of a beating heart to exemplify the change of X with time t. Those skilled in the art will be able to adapt the description, mutatis mutandis, for other periodic and non-periodic changes of X with time.

Returning to FIG. 1, detector 44 comprises an electrocardiograph (ECG) sensor, and PU 24 uses an output of the ECG to synchronize counts $\{y_b\}$ with different stages of the beating heart so as to cover a complete heat beat, i.e., between end-systolic and end-diastolic states. PU 24 uses the ECG output to divide counts $\{y_b\}$ into N time slots $\{t=0, 1, 2, \ldots,$ N−1}, where N is a positive integer, and PU 24 sums the values of the counts for each specific bin b to give N different values $\{y_{b0}, y_{b1}, \ldots y_{b(N-1)}\}$. In an embodiment of the present invention, N may be chosen to be equal to $2^n$, where n is a positive integer, although any other convenient value of N, for example 24, may be used.

Taking account of the time dependence of X, equation (20) may be rewritten:

$$-\log[P(X \mid Y)] = \sum_{t=0}^{N-1} \left( \frac{1}{2} \sum_{b=1}^{b_M} \frac{(y_b - (HX)_b)^2}{\max(y_b, B)} + \frac{1}{\sigma} \sum_s \sum_i \frac{\|(\theta_i^s - \alpha_s \theta_i^{s+1})\|_2}{s} \right) + \qquad (23)$$

$$\sum_i W(\{x_i(t), t = 0, 1, \ldots N-1\})$$

where the expressions $$\frac{\|(\theta_i^s - \alpha_s \theta_i^{s+1})\|_2}{s}$$

and $$\frac{(y_b - (HX)_b)^2}{\max(y_b - B)}$$

are evaluated separately for each time slot t;

$\{x_i(t), t=0, 1, 2, \ldots N−1\}$ are the sets of $x_i$ at time slots t; and

W(.) is a suitable one-dimensional regularization function.

In one embodiment of the present invention, $W_{(\ )}$ is expressed in terms of a Fourier transform of $x_i(t)$, and is defined as:

$$W(\{x_i(t), t = 0, 1, \ldots, N-1\}) = \sum_{k=0}^{N-1} \tilde{g}_i(\omega_k) |\tilde{x}_i(\omega_k)|^2 \qquad (24)$$

where $\{\tilde{x}_i(\omega_k), k=0, 1, \ldots, N−1\}$ is the 1-dimensional Fourier transform of the sequence $\{x_i(t), t=0, 1, \ldots, N−1\}$;

$$\omega_k = \frac{2\pi k}{N}; \text{ and}$$

$\tilde{g}_i(\omega_k)$ are N filtering constants (for every i), typically determined as described above with respect to FIG. 3 for B, σ.

In an alternative embodiment, W(.) is a one-dimensional expression based on equation (19):

$$W(\{x_i(t), t = 0, 1, \ldots N-1\}) = \frac{1}{\sigma_t} \sum_{s=1}^{N/2} \sum_{k=0}^{N-1} \frac{\left\| \begin{pmatrix} \theta_i^s(k) - \\ \alpha_s \theta_i^{s+1}(k) \end{pmatrix} \right\|_2}{s} \qquad (25)$$

where N is assumed to be even;

$$\alpha_s = \frac{s^2}{(s+1)^2};$$

and $$\theta_i^s(k) = \sum_{m=0}^{s-1} x_i(k+m) - \sum_{m=-s}^{-1} x_i(k+m).$$

Further alternatively, W(.) may be defined based on the assumption that results follow a Laplacian distribution similar to that described in the papers of Mallat and Simoncelli et al. referenced in the Background of the Invention. For example, $$W(\{x_i(t), t = 0, 1, \ldots, N-1\}) = \frac{1}{\sigma_t} \sum_{k=0}^{N-1} |x_i(k) - x_i(k+1)|^{r_t} \qquad (26)$$

or $$W(\{x_i(t), t = 0, 1, \ldots, N-1\}) =$$

$$\frac{1}{\sigma_t} \sum_{k=0}^{N-1} |x_i(k-1) - 2x_i(k) + x_i(k+1)|^{r_t}$$

In equations (25) and (26), since $\{x_i\}$ are assumed to be periodic and are measured in N repeating time slots, $x_i(k)$ is to be considered as $x_i(k \bmod N)$. Also in the equations, $\sigma_t$ and $r_t$ are constants which are typically determined as described above with respect to FIG. 3.

Other expressions for W(.) will be apparent to those skilled in the art, and are comprised within the scope of the present invention.

Figure 5:
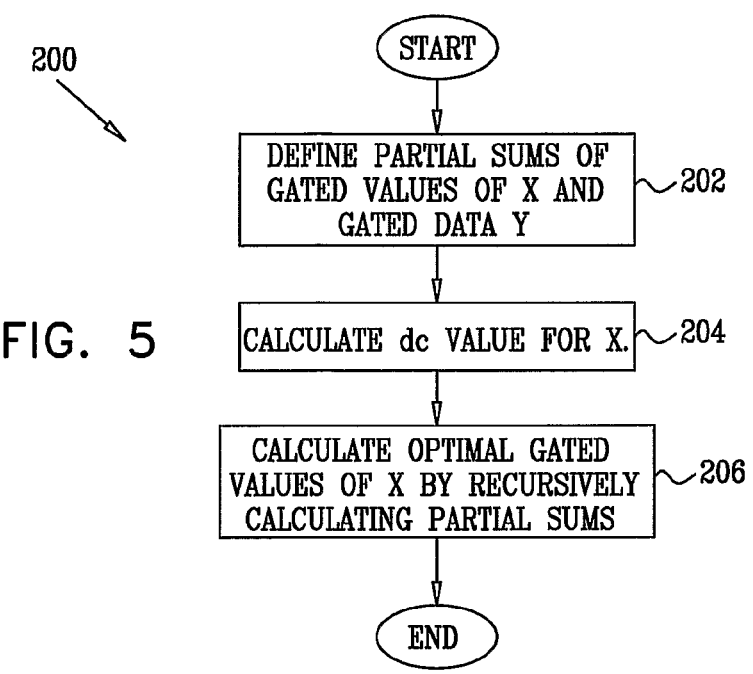
FIG. 5 is a flowchart illustrating steps for determining gated values of an image generated in the system of FIG. 1, according to an embodiment of the present invention.

FIG. 5 is a flowchart 200 showing steps for finding gated values of X, assuming W(.) is of the form given by equation (24), according to an embodiment of the present invention.

From equation (21), a function $\Phi^{3D}(X,Y,B,\sigma)$ is defined:

$$\Phi^{3D}(X, Y, B, \sigma) \equiv (-\log[P(X \mid Y)] = \qquad (27)$$

$$\frac{1}{2} \sum_{b=1}^{b_M} \frac{(y_b - (HX)_b)^2}{\max(y_b, B)} + \frac{1}{\sigma} \sum_{s=1}^{s=5} \sum_{i \in Z^3} \frac{\|(\theta_i^s - \alpha_s \theta_i^{s+1})\|_2}{s}.$$

In a first step 202, the following partial sums of the gated values of X, and partial sums of gated data Y, are defined:

$$X^{(l)}(\tau) \equiv \sum_{\tau'=0}^{2^{n-l}-1} X(\tau + 2^l \tau') \qquad (28)$$

$$Y^{(l)}(\tau) \equiv \sum_{\tau'=0}^{2^{n-l}-1} Y(\tau + 2^l \tau')$$

where $0 \le l \le n$, $0 \le \tau < 2^l$, n, l, and τ are 0 or positive integers. Herein, by way of example, n is assumed equal to 3.

The parameter l in equations (28) corresponds to a level of partial sum. Thus, for n=3, the highest value of l is 3 and each partial sum is one term corresponding to a gated value, e.g., $X^{(3)}(2) \equiv X(2)$. For l=1, there are four terms in each partial sum of gated values, e.g., $X^{(1)}(0) \equiv X(0)+X(2)+X(4)+X(6)$.

In a second step 204, a "dc" value for X, $X_{dc}$, corresponding to the value of X calculated from the total values in each bin b of $y_b$, is computed. In addition, an optimal value $\hat{X}^{(0)}(0)$ is defined.

$$X_{dc} = \underset{\{0 \leq x'_i, i \in Z^D\}}{\arg\min}\, \Phi^{3D}(X'; Y^{(0)}(0); B, \sigma) \quad (29)$$

$$\hat{X}^{(0)}(0) \equiv X_{dc} \quad (30)$$

It will be understood that step 204 corresponds to evaluating equation (21).

In a third step 206, optimal values of $\hat{X}^{(1)}(\tau)$, $0 \leq \tau < 2^{l-1}$, are evaluated recursively, for l=1, 2, 3, as follows:

$$\left\{\begin{array}{l}\hat{X}^{(l)}(\tau), \\ 0 \leq \tau < 2^{l-1}\end{array}\right\} = \underset{\left\{\begin{array}{c}0 \leq x_i^{(l)}(\tau) \leq \hat{x}_i^{(l-1)}(\tau), i \in Z^3, \\ 0 \leq \tau < 2^{l-1}\end{array}\right\}}{\arg\min}$$

$$\Phi^{(l)}\!\left(\left\{\begin{array}{c}X^{(l)}(\tau), \\ 0 \leq \tau < 2^{l-1}\end{array}\right\}; \begin{array}{c}Y^{(l)}, \\ \hat{X}^{(l-1)}\end{array}\right)$$

where $$\Phi^{(l)}\!\left(\left\{\begin{array}{c}X^{(l)}(\tau), \\ 0 \leq \tau < 2^{l-1}\end{array}\right\}; \begin{array}{c}Y^{(l)}, \\ \hat{X}^{(l-1)}\end{array}\right) \equiv \quad (31)$$

$$\sum_{k=0}^{2^{l-1}-1}\left\{\Phi^{3D}\!\left(\begin{array}{c}X^{(l)}(k); \\ Y^{(l)}(k); \\ \frac{B}{2^l}, \sigma\end{array}\right) + \Phi^{3D}\!\left(\begin{array}{c}\hat{X}^{(l-1)}(k) - X^{(l)}(k); \\ Y^{(l)}(k+2^{l-1}); \\ \frac{B}{2^l}, \sigma\end{array}\right)\right\} +$$

$$2^l \sum_{k=0}^{2^l-1} \tilde{g}(\omega_k^{(l)})|\tilde{X}^{(l)}(\omega_k^{(l)})|^2 \text{ for } \omega_k^{(l)} = \frac{2\pi k}{2^l},\, 0 \leq k < 2^l.$$

Using the values determined in equations (29) and (30), the additional optimal values $\hat{X}^{(l)}(\tau+2^{l-1})$, $0 \leq \tau < 2^{l-1}$ are evaluated as follows:

$$\hat{X}^{(l)}(\tau+2^{l-1}) = \hat{X}^{(l-1)}(\tau) - \hat{X}^{(l)}(\tau),\, 0 \leq \tau \leq 2^{l-1} \quad (32)$$

FIGS. 6A, 6B, 7A, and 7B show schematic images of phantoms. The images shown in FIGS. 6A and 7A were created using an ordered-subsets expectation maximization (OSEM) algorithm, as is known in the art. The images in FIGS. 6B and 7B were computed using equation (21), according to an embodiment of the present invention. For all images, phantoms were constructed by embedding six hollow or solid spheres, having diameters ranging from 9.5 mm to 31.8 mm, in a cylinder. A first "hot spheres" phantom (FIGS. 7A, 7B) was constructed by filling the cylinder and hollow spheres with aqueous solutions of a radiochemical using $^{99m}$Tc. The concentration of the solution in the spheres was twice the concentration of the solution in the cylinder. A second "cold spheres" phantom (FIGS. 6A, 6B) was constructed in which solid non-radioactive spheres were used. For both phantoms, two-dimensional cross-sectional images were generated from one set of data taken by a camera having a collimator with parallel-sided channels.

Figures 6A, 6B:
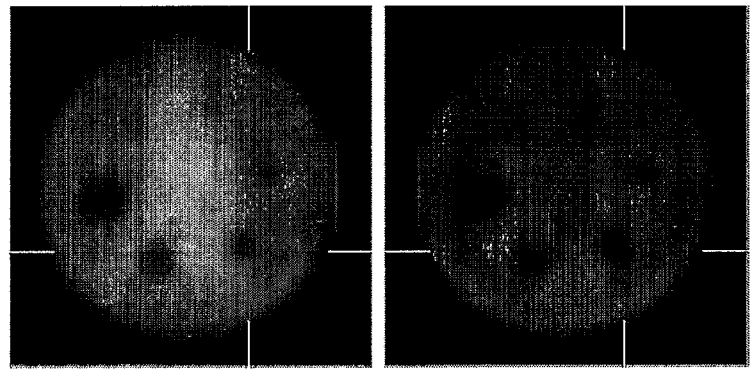
FIGS. 6A and 6B shows schematic images of "cold sphere" phantoms.
Figures 7A, 7B:
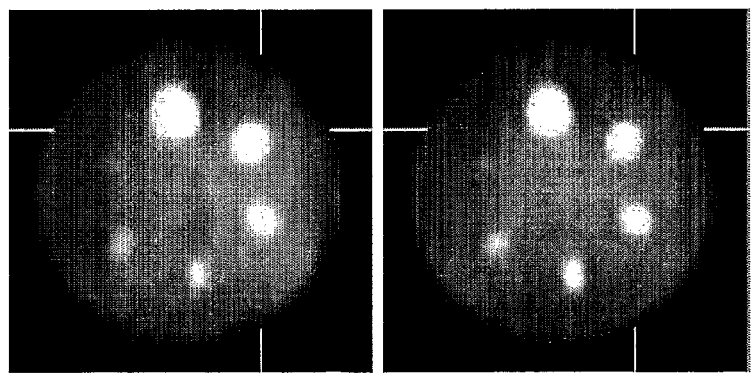
FIGS. 7A and 7B shows schematic images of "hot sphere" phantoms.

Comparison of the images of FIGS. 6A, 7A with the images of FIGS. 6B, 7B illustrates a number of advantages of embodiments of the present invention:

The imaged radiochemical concentration in the cylinder, for both types of phantom, is significantly more uniform in FIGS. 6B and 7B than in FIGS. 6A and 7A.

The ratio of radiochemical concentrations for the spheres and for the cylinder is closer to the actual values in the images of FIGS. 6B and 7B, compared to the image of FIGS. 6A and 7A.

The images of the spheres in FIGS. 6B and 7B are significantly sharper than the corresponding images in FIGS. 6A and 7A.

The contrast between the imaged spheres and the cylinder in FIGS. 6B and 7B is significantly greater than that between the corresponding images in FIGS. 6A and 7A. Taken together with the other differentiating factors described above, this leads to the smallest sphere being very difficult to see in FIGS. 6A and 7A, whereas it is clearly visible in FIGS. 6B and 7B.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for imaging, comprising:
   counting quanta of energy emitted into a range of angles from particles of an energy emitter distributed over a volume in a body, thereby generating a set of counts;
   defining a probability distribution expression that specifies a local concentration of the particles of the energy emitter over the volume as a function of the set of counts, the function being defined in terms of respective coefficients of a plurality of different scales of the local concentration, comprising at least a first and a second scale;
   specifying a dependence of the coefficients of the first scale on the coefficients of the second scale; and
   computing the local concentration over the volume by applying the probability distribution expression to the set of counts subject to the specified dependence,
   the dependence being given by:

$$\alpha_s = \frac{s^2}{(s+n)^2}$$

wherein s represents a cardinality of the first scale, $0.5 \leq n < 1.5$, and wherein $\alpha_s$ represents the dependence.

2. The method according to claim 1, wherein the dependence comprises a first cardinality of the first scale.

3. The method according to claim 2, wherein the dependence comprises a second cardinality of the second scale.

4. The method according to claim 1, wherein the first scale and the second scale comprise sequential scales.

5. The method according to claim 1, wherein an argument of the function comprises a term:

$$(\theta_i^s - \alpha_s \theta_i^{s+1}),$$

wherein:
i is an index of a location of the particles;
s and s+1 are respective cardinalities of the first and second scales;
$\theta_i^s, \theta_i^{s+1}$ represent respective coefficients of the first and second scales; and
$\alpha_s$ is a function of s.

6. The method according to claim 1, wherein $$f_s(z) = \frac{|||z||_2|^r}{s^r \sigma}$$

wherein:
$f_s(z)$ represents the function, having an argument z;
s is a cardinality of the first scale;
r is a positive number; and
σ is a constant.

7. The method according to claim 6, wherein $$z = (\theta_i^s - \alpha_s \theta_i^{s+1}),$$

wherein:
i is an index of a location of the particles;
s+1 is a cardinality of the second scale;
$\theta_i^s, \theta_i^{s+1}$ represent respective coefficients of the first and second scales; and
$\alpha_s$ is a function of s.

8. The method according to claim 1, wherein the probability distribution expression comprises a term $-\log[P(X)]$, wherein $$-\log[P(X)] = \sum_s \sum_i f_s(\theta_i^s - \alpha_s \theta_i^{s+1}),$$

and wherein:
X is a vector representing the local concentration;
$f_s(.)$ represents the function;
i is an index of a location of the particles;
s and s+1 are respective cardinalities of the first and second scales;
$\theta_i^s, \theta_i^{s+1}$ represent respective coefficients of the first and second scales; and
$\alpha_s$ is a function of s.

9. The method according to claim 1, wherein the probability distribution expression comprises a term $-\log[P(Y|X)]$, wherein $$-\log[P(Y|X)] = \frac{1}{2} \sum_{b=1}^{b_M} \frac{(y_b - (HX)_b)^2}{\Delta_b},$$

and wherein:
b is an index representing bins receiving the set of counts;
$b_M$ is a total number of the bins;
$y_b$ is a count received at a bin b;
$(HX)_b$ is an expected number of counts for the bin b Y is a vector representing the set of counts;
X is a vector representing the local concentration; and
$\Delta_b$ is a variance for the bin b.

10. The method according to claim 9, wherein $\Delta_b = \max(y_b, B)$, wherein B is a constant.

11. The method according to claim 1, wherein the probability distribution expression comprises a term having a distribution chosen from a Poisson distribution, a Laplacian distribution, and a non-white Gaussian distribution.

12. The method according to claim 1, wherein the coefficients comprise wavelet coefficients of a Haar wavelet.

13. The method according to claim 1, wherein computing the local concentration comprises performing an iteration on the probability distribution expression to find a maximum value of a probability distribution comprised in the expression.

14. The method according to claim 1, wherein the local concentration comprises a plurality of time-dependent-local-concentrations comprising a first time-dependent-local-concentration measured at a region of the volume during a first time slot and a second time-dependent-local-concentration, different from the first time-dependent-local-concentration, measured at the region during a second time slot, and wherein the probability distribution expression comprises a time-dependent regularization function relating the first time-dependent-local-concentration and the second time-dependent-local-concentration.

15. The method according to claim 14, wherein the time-dependent regularization function comprises a Fourier transform of a sequence of time-dependent-local-concentrations at the region, the sequence comprising the first time-dependent-local-concentration and the second time-dependent-local-concentration.

16. The method according to claim 14, and comprising synchronizing at least one of the first time slot and the second time slot in response to a time-dependent signal received from the body.

17. The method according to claim 14, wherein computing the time-dependent-local-concentrations comprises iteratively computing partial sums of the time-dependent-local-concentrations.

18. The method according to claim 1, wherein the plurality of different scales comprises a number of scales chosen from between three and seven scales.

19. The method according to claim 18, wherein the number of scales comprises five scales.

20. The method according to claim 1, wherein the probability distribution expression comprises a conditional expectation.

21. Imaging apparatus, comprising:
a camera which is arranged to count quanta of energy emitted into a range of angles from particles of an energy emitter distributed over a volume in a body, thereby generating a set of counts; and
a processing unit which is configured to:
define a probability distribution expression that specifies a local concentration of the particles of the energy emitter over the volume as a function of the set of counts, the function being defined in terms of respective coefficients of a plurality of different scales of the local concentration, comprising at least a first and a second scale,
specify a dependence of the coefficients of the first scale on the coefficients of the second scale, and compute the local concentration over the volume by applying the probability distribution to the set of counts subject to the specified dependence,
the dependence being given by:

$$\alpha_s = \frac{s^2}{(s+n)^2}$$

wherein s represents a cardinality of the first scale, $0.5 \leq n < 1.5$, and wherein $\alpha_s$ represents the dependence.

22. The apparatus according to claim 21, wherein the local concentration comprises a plurality of time-dependent-local-concentrations comprising a first time-dependent-local-concentration measured at a region of the volume during a first time slot and a second time-dependent-local-concentration, different from the first time-dependent-local-concentration, measured at the region during a second time slot, the apparatus comprising:
a detector which detects a time-dependent signal from the body and which conveys the time-dependent signal to the processing unit so as to synchronize at least one of the first time slot and the second time slot.

23. A computer software product stored on a non-transitory computer readable medium for imaging, comprising the computer-readable medium having computer program instructions recorded therein, which instructions, when read by a computer, cause the computer to:
receive counts of quanta of energy emitted into a range of angles from particles of an energy emitter distributed over a volume in a body, thereby generating a set of counts,
define a probability distribution expression that specifies a local concentration of the particles of the energy emitter over the volume as a function of the set of counts, the function being defined in terms of respective coefficients of a plurality of different scales of the local concentration, comprising at least a first and a second scale,
specify a dependence of the coefficients of the first scale on the coefficients of the second scale, and
compute the local concentration over the volume by applying the probability distribution expression to the set of counts subject to the specified dependence,
the dependence being given by:

$$\alpha_s = \frac{s^2}{(s+n)^2}$$

wherein s represents a cardinality of the first scale, $0.5 \leq n < 1.5$, and wherein $\alpha_s$ represents the dependence.

* * * * *